United States Patent [19]

McConnell

[11] Patent Number: 4,496,522
[45] Date of Patent: Jan. 29, 1985

[54] VERTICAL DECONTAMINATION BATH FOR FIBRESCOPES

[76] Inventor: Louise McConnell, 10 Terrasse Goyer, Deux Montagnes, Quebec, Canada, H7R 4W1

[21] Appl. No.: 482,314

[22] Filed: Apr. 1, 1983

[51] Int. Cl.³ .......................... A61L 2/18; A61L 2/26; B08B 9/00; A47K 3/11
[52] U.S. Cl. ................................ 422/300; 134/22.11; 248/311.2
[58] Field of Search .................... 422/300, 301; 128/6; 134/113, 166 R, 201, 22.11; 248/311.2

[56] References Cited

U.S. PATENT DOCUMENTS

| | | | |
|---|---|---|---|
| 2,805,454 | 9/1957 | Ihrig | 422/300 |
| 3,321,068 | 5/1967 | Beach | 422/300 X |
| 3,488,141 | 6/1970 | Hausing | 422/300 |
| 3,511,592 | 12/1970 | Tuma | 422/300 |
| 3,963,438 | 6/1976 | Banez | 134/22.11 X |
| 4,262,800 | 4/1981 | Nethercutt | 206/45.34 X |
| 4,403,605 | 9/1983 | Tanikawa | 128/6 |

FOREIGN PATENT DOCUMENTS

| | | | |
|---|---|---|---|
| 0038168 | 10/1981 | European Pat. Off. | 422/292 |
| 0072257 | 2/1983 | European Pat. Off. | 422/292 |
| 2094150 | 9/1982 | United Kingdom | 422/292 |
| 0741884 | 6/1980 | U.S.S.R. | 422/301 |

*Primary Examiner*—Barry S. Richman
*Assistant Examiner*—Brion P. Heaney

[57] ABSTRACT

A decontaminator bath for fibrescopes, including a flat, rigid and upright plate supporting four brackets, namely: a light source tube support bracket with a horizontal cylindrical portion, a control section support bracket and upper and lower bath tube support brackets, the latter three brackets being vertically spaced apart and vertically aligned; and a straight rigid and hollow bath tube having an open top end and a sealed bottom end.

6 Claims, 2 Drawing Figures

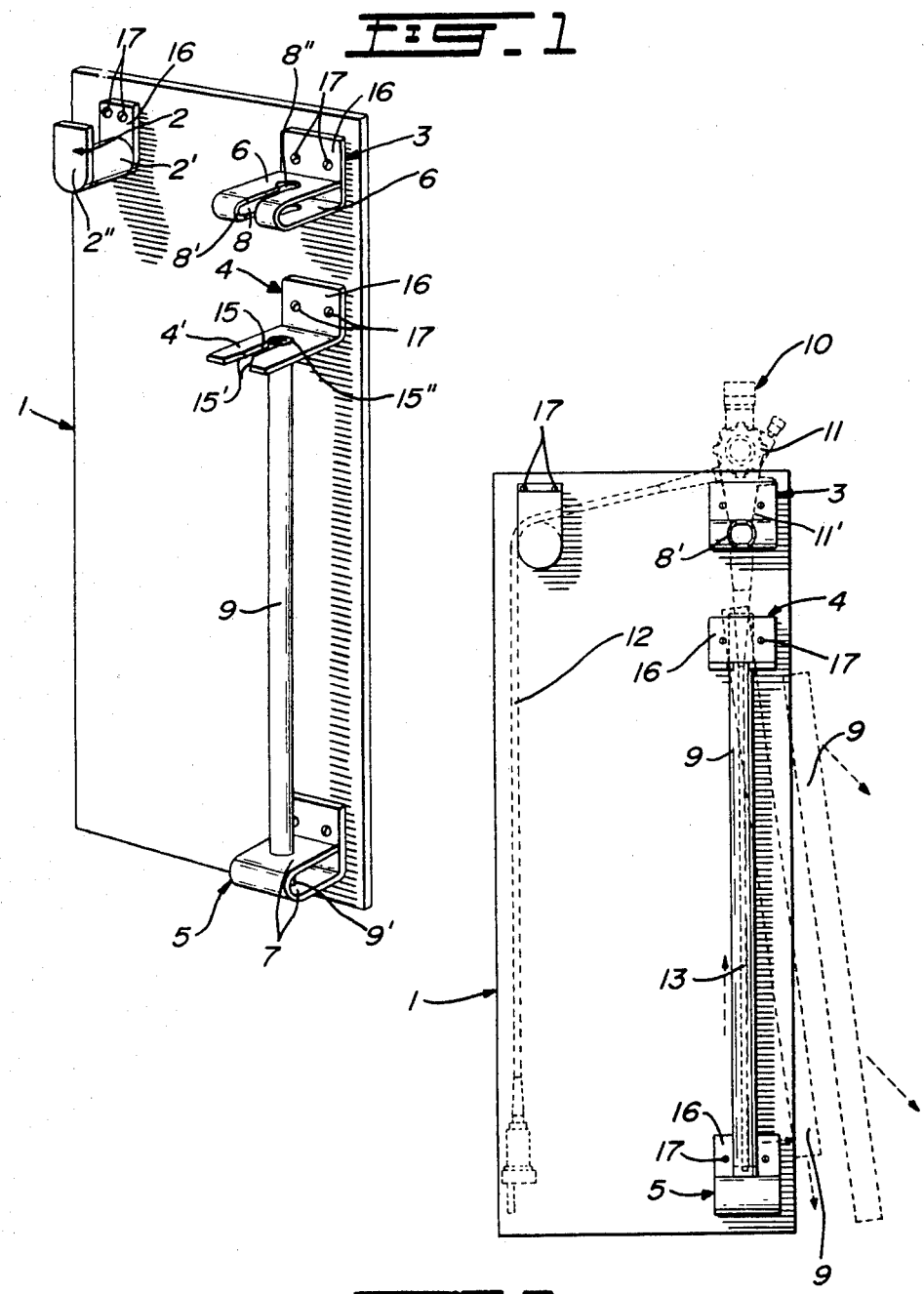

VERTICAL DECONTAMINATION BATH FOR FIBRESCOPES

FIELD OF THE INVENTION

The present invention relates to a tube sterilizing device in combination with support means, more specifically to a sterilizer and support for optical fibrescopes used in modern diagnostic and exploratory medicine.

BACKGROUND OF THE INVENTION

The use of "fibrescopes", i.e. devices such as bronchoscopes, duodenoscopes etc. having a control section, an insertion tube and a light source tube, has increased dramatically in modern medicine over the past few years. However, many hospitals have experienced difficulty in storing fibrescopes both because it is necessary to keep the latter in upright position as much as possible to avoid damage to the control section, as well as the fact that both the insertion tube and the light source tube are flexible only to a limited extent and must therefore be kept as straight as possible. (The terms "insertion tube" and "light source tube" referred to herein-after designate the tube or appendage adapted to be inserted into the human body and the tube containing flexible optical fibres, respectively). In addition, the insertion tube must of course be sterilized before and after each use.

OBJECT OF THE INVENTION

Accordingly it is a prime object of the present invention to provide, in combination, a support means and a decontaminating or sterilizer bath for fibrescopes.

It is another important object of the present invention to provide a bath of the above type which is very simple in design and construction.

It is still another object of the present invention to provide a bath of the above type which may be removed for emptying and refilling.

It is yet another object of the present invention to provide a device of the above type which ensures positive vertical support for a fibrescope and its appendages.

SUMMARY OF THE INVENTION

The above and other objects of the present invention are realized according to a preferred embodiment comprising an assembly of brackets adapted to be secured to a wall or other convenient vertical support surfaces such as a rigid flat plate adapted to be fixed in upright position. The brackets include a light source tube support bracket, a control section support bracket and upper and lower bath tube support brackets. The first named bracket has a round horizontal surface which is of a larger radius than the minimum radius of curvature the light source tube can be bent to without damaging it. The control section support bracket is horizontally spaced-apart from the light source tube support bracket and has at least one horizontal surface in which is formed an outwardly-extending slot. The slot is adapted to receive the upper end of the insertion tube and the control section thereby rests on the bracket. The upper bath tube support bracket is spaced downwardly from the control section support bracket and is vertically aligned with the same. This upper bath tube support bracket also has a forwardly extending slot with an enlarged rear end portion in which is removably inserted the top end of the bath tube. The latter consists of a straight, rigid and hollow cylindrical tube having an open top end and a closed bottom end. The bath tube is to be filled with a sterilizer solution. The lower bath support bracket supports the base or bottom end of the bath tube. It is in vertical alignment with the upper bath tube support bracket being spaced downwardly from the same. It is adapted to removably retain the bath tube.

BRIEF DESCRIPTION OF THE DRAWINGS

The above will be more clearly understood by having referral to the preferred embodiment of the invention, illustrated by way of the accompanying drawings, in which:

FIG. 1 is a perspective view of the invention, and

FIG. 2 is a front elevation of the invention, also showing in dashed outline the fibrescope and the bath sterilizer tube in removing positions.

Like numerals refer to like elements throughout the drawings.

DETAILED DESCRIPTION OF THE INVENTION

The brackets of the invention are fixed to a flat rigid upright plate 1 having a generally rectangular shape and having its longer dimension disposed vertically. Plate 1 can be affixed to a wall or other vertical structure (not shown) whether this structure is fixed or mobile.

Referring to FIG. 2 a typical fibrescope 10 is shown having a control section 11, a light source tube 12 and an insertion tube 13; as illustrated therein the light source tube 12 is supported in vertical position in the following manner: a light source tube support bracket 2 is secured to plate 1 in its upper left-hand corner. Bracket 2 has a forwardly projecting cylindrical portion 2' which is of larger radius than the minimum radius of curvature allowed the light source tube 12 without incurring damage thereto. Bracket 2 is further provided with a front vertical flange 2" to prevent light source tube 12 from slipping off the bracket.

Referring also to FIG. 1 the invention further comprises three more support brackets; a control section support bracket 3, an upper bath tube support bracket 4 and a lower bath tube support bracket 5. All three brackets 3, 4 and 5 are spaced vertically apart on plate 1 and are also vertically aligned. Topmost bracket 3 is horizontally spaced from bracket 2.

Control section bracket 3 and bracket 5 are each formed preferably of one piece of material which is bent at 180° degrees thus defining a pair of vertically-spaced horizontal surfaces 6 and 7 respectively.

Bracket 3 is made with a forwardly extending slot 8 in both surfaces 6. The edges 8' of slot 8 are rounded (as seen clearly in FIG. 2) to permit easy insertion of the lower portion 11' of control section 11 therein. The rear end 8" of slot 8 is wider than the rest of the latter and is circular in the horizontal plane.

The top surface 7 of bracket 5 is provided with a hole adapted to receive the lower end 9' of a rigid, straight and hollow bath tube 9. The latter has an open top end while the bottom is sealed, and is adapted to contain an appropriate sterilizing solution. The bottom end of bath tube 9 rests on the lower surface 7 of bracket 5.

Bracket 4 is formed with a single outwardly-projecting flange 4'. The latter has a second slot 15 provided with slightly flared outer edges 15' and a wider circular rear end 15".

It is to be noted that all four brackets 2, 3, 4 and 5 are each secured to plate 1 by means of an integrally formed vertical flange 16 and screws 17 although other securing means could be provided. It should also be noted that plate 1 could be dispensed and the four brackets directly secured to a wall or other vertical support in the above described configuration.

Also, each bracket is preferably made of rigid non-abrasive material such as acrylic.

The manner of using the device of the present invention is clearly shown in FIG. 2: control section 11 of the fibrescope is inserted into bracket 3, the light source tube 12 is supported over bracket 2 and the insertion tube 13 extends downwardly into the bath tube 9. Thus a stable and conveniently usable support and decontaminator is obtained.

FIG. 2 also illustrates how bath tube 9 can be removed for emptying and refilling and when it is not required its bottom end is pushed upwardly until the latter clears the top surface 7 of bracket 5. Then the bottom end is tilted outwardly and lowered to disengage the top end from bracket 4.

When bath tube 9 is not used, portion 11 and insertion tube 13 can be inserted through slots 8 and 15 of brackets 3 and 4. It is to be understood that the relative locations of the brackets on the support can vary to accomodate various designs of fibrescopes.

What I claim is:

1. A decontamination bath and support assembly for fibrescopes of the type having a light source tube, a control section and an insertion tube, wherein the bath and support assembly comprises a light source tube support bracket having a round top portion of greater radius of curvature than that to which a light source tube can be bent without damage; a control section support bracket; a straight, rigid, and hollow bath tube adapted to contain a sterilization solution wherein said bath tube has an open top end and a sealed bottom end; an upper bath tube support bracket; a lower bath tube support bracket; and means for supporting said control section bracket, said upper bath tube bracket and said lower bath tube bracket in vertically spaced-apart and vertically-aligned relation for removably supporting said bath tube between said upper and lower bath tube brackets, said light source tube bracket being supported on said support means in horizontally-spaced relation from said control section support bracket whereby a fibrescope may be supported thereon with a light source tube thereof supported on said light source tube bracket, the fibrescope control section supported on top of said control section bracket, and the fibrescope insertion tube inserted within said bath tube.

2. A decontamination bath and support assembly as defined in claim 1 wherein said light source tube support bracket is provided with a vertical flange at its outer end.

3. A decontamination bath and support assembly as defined in claim 1 wherein said control section bracket and said lower bath tube bracket each have two vertically spaced-apart horizontal surfaces.

4. A decontamination bath and support assembly as defined in claim 3 wherein said horizontal surfaces of said control section bracket are each formed with a forwardly extending and forwardly opening slot; each said slot having a wider circular rear end.

5. A decontamination bath and support assembly as defined in claim 4 wherein said upper bath tube support bracket has one forwardly extending flange; said flange being provided with a second forwardly opening slot which has a wider, circular rear end.

6. A decontamination bath and support assembly as defined in claim 5, wherein the upper surface of said horizontal surfaces of said lower bath tube bracket is provided with means defining a hole for receiving said bath tube, wherein when said bath tube is supported by said bath tube brackets said bottom end of said bath tube rests on the lower surface of said horizontal surfaces of said lower bath tube bracket and the upper end of said bath tube engages the circular rear end of said second slot of said upper bath tube support bracket.

* * * * *